US005459568A

United States Patent [19]
Yano et al.

[11] Patent Number: 5,459,568
[45] Date of Patent: Oct. 17, 1995

[54] CONCENTRATION MEASURING APPARATUS

[75] Inventors: Saihei Yano, Narashino; Masaya Yano, Misato, both of Japan

[73] Assignees: Tomoe Engineering Co., Ltd.; Automatic System Research Co., Ltd., both of Tokyo, Japan

[21] Appl. No.: 211,576

[22] PCT Filed: Aug. 24, 1993

[86] PCT No.: PCT/JP93/01179

§ 371 Date: Apr. 25, 1994

§ 102(e) Date: Apr. 25, 1994

[87] PCT Pub. No.: WO94/04908

PCT Pub. Date: Mar. 3, 1994

[30] Foreign Application Priority Data

Aug. 24, 1992 [JP] Japan .................. 4-224025
Jun. 21, 1993 [JP] Japan .................. 5-149154

[51] Int. Cl.$^6$ ............................... G01N 21/85
[52] U.S. Cl. ............................ 356/336; 356/442
[58] Field of Search ...................... 356/436, 440, 356/442, 410, 441; 250/901

[56] References Cited

U.S. PATENT DOCUMENTS 5,104,228  4/1992  Baillie ..................... 356/442

*Primary Examiner*—Richard A. Rosenberger
*Attorney, Agent, or Firm*—Kanesaka & Tekeuchi

[57] ABSTRACT

A concentration measurement apparatus capable of accurately measuring the concentration of suspended matter in a liquid is provided.

A transmitter 1 which transmits sound waves, light waves, or the like, and a receiver 2, which is disposed in opposition to this transmitter 1, are provided, small pipes 3 and 4, which enclose the transmitting surface position of the transmitter and the receiving surface position of the receiver, and which are opened in the direction of transmission and the direction of reception, respectively, are provided, and a mechanism for filling these small pipes with a clean liquid or gas is provided.

The transmitting surface of the transmitter and the receiving surface of the receiver are not contaminated by means of the deposition or generation of suspended matter, so that it is possible to conduct the accurate measurement of the concentration in a constant manner.

5 Claims, 3 Drawing Sheets

CONCENTRATION MEASURING APPARATUS

TECHNICAL FIELD

The present invention relates to a concentration measuring apparatus which measures the concentration of matter in a suspension or liquid which is the object of the measurement, which employs sound waves or light waves, and in further detail, relates to an improvement in a concentration measurement apparatus which has a liquid having suspended matter uniformly suspended therein as an object of measurement. The apparatus has a transmitter for transmitting sound waves or light waves in the liquid which is the object of measurement, and a receiver which receives the sound waves or light waves which are transmitted by the transmitter. The apparatus measures the concentration of the suspended matter present in the liquid which is the object of measurement, by means of measuring, at the receiver, the amount of attenuation or the amount of scattering of the sound waves or light waves which are transmitted from the transmitter in the direction of the matter suspended in the liquid which is the object of measurement.

BACKGROUND ART

Various concentration measuring apparatuses have previously been developed which place a transmitter and a receiver in a substance to be measured, transmit sound waves or light waves from the transmitter in the direction of the matter suspended in the liquid constituting the object of measurement, and measure the amount of attenuation or amount of scattering thereof at the receiver, to thereby measure the concentration of suspended matter in the substance which is to be measured.

In the conventional apparatuses described above, the transmitting surface of the transmitter and the receiving surface of the receiver are in direct contact with the liquid which is the substance to be measured, so that a material such as suspended matter present in the substance which is to be measured, or matter which is dissolved in the substance to measured or is present as impurities therein is deposited or generated thereon, and thereby, the transmitting surface of the transmitter and the receiving surface of the receiver are contaminated.

The contamination as a result of deposition or generation on the transmitting surface or the receiving surface as described above alters the amount of transmission, amount of attenuation, amount of scattering, and the like of the sound waves or light waves, and causes errors in the measured values, so that it becomes impossible to make accurate concentration measurements. Thus, particularly, in concentration measurement apparatuses which are used under conditions of severe contamination, it is necessary to remove the contaminants deposited on the transmitting surface and the receiving surface. Conventionally, methods for the removal of contaminants deposited or generated thereon have included methods which mechanically remove deposited matter, such as manual cleaning, washing with water, or washing in the presence of ultrasonic waves.

Removal methods for deposited matter which were conventionally adopted, with the exception of the case in which manual cleaning was conducted, a mechanism in which washing was automatically conducted. However, the use of such automatic washing mechanisms is not necessarily sufficient, and in particular, in applications having as the object thereof substances to be measured in which contaminants are easily deposited, such as sewage sludge and the like, the reliability of the values measured by means of a concentration meter employing the amount of attenuation or the amount of scattering in sound waves or light waves must of necessity be rather low. Furthermore, in a manual cleaning, as the pace of contamination, is faster, the troublesome of the cleaning can not be avoided, and there is a problem in that continuous measurement cannot be attained.

The present invention has as an object thereof to provide a concentration measurement apparatus which is capable, even in applications in which contaminants are easily deposited, such as when sewage sludge is the object of the measurement as described above, of accurately measuring the concentration of suspended matter present in a substance to be measured by means of providing a method by which contamination is not deposited or generated on the transmitting surface of the transmitter or on the receiving surface of the receiver, and by transmitting a stipulated amount of sound waves or light waves in the direction of matter suspended in a liquid which is to be measured, and receiving the amount of attenuation or amount of scattering thereof in a manner unaffected by the contamination.

DISCLOSURE OF THE INVENTION

In order to achieve the above object, the concentration measurement apparatus in accordance with the present invention has a liquid having suspended matter uniformly suspended therein as the object of measurement, and is provided with a transmitter which transmits sound waves, light waves, or the like in the substance to be measured, and a receiver, which receives the sound waves, light waves, or the like which are transmitted by the transmitter. The apparatus measures, at the receivers, the amount of attenuation or the amount of scattering of the sound waves, light waves, or the like, transmitted by the transmitter in the direction of the suspended matter present in the liquid which is to be measured, and thereby measures the concentration of suspended matter present in the substance to be measured. Enclosed spaces are provided which enclose the position of the transmitting surface of the transmitter and the position of the receiving surface of the receiver and which open in the direction of transmission and the direction of reception, respectively, and a mechanism is provided for filling these enclosed spaces with a clean liquid or gas.

in the concentration measurement apparatus in accordance with the present invention, the transmitting surface position of the transmitter and the receiving surface position of the receiver are enclosed by enclosed spaces which are opened in the direction of transmission and the direction of reception, respectively, and these enclosed spaces are normally filled with a clean liquid or gas, so that the transmitting surface of the transmitter and the receiving surface of the receiver do not come into direct contact with the substance which is to be measured, and accordingly, the contamination of the transmitting surface and the receiving surface by means of the deposition or generation of suspended matter is completely prevented.

In accordance with the present invention, contaminants are not deposited or generated on the transmitting surface of the transmitter or the receiving surface of the receiver, so that it is possible to accurately measure the concentration of suspended matter. The amount of transmission, amount of attenuation, amount of scattering, and the like, of the sound waves, light waves, or the like are unaffected by contamination.

BEST MODE FOR CARRYING OUT THE INVENTION

With respect to the executed mode in accordance with the present invention, in which the transmitting surface position of the transmitter and the receiving surface position of the receiver are respectively enclosed, the small pipes constituting the enclosed spaces which are opened in the direction of transmission and the direction of reception, respectively, are filled with clean liquid or gas, and the transmitting and receiving surfaces are thus not placed in direct contact with the substance to be measured, an explanation will be given hereinbelow with reference to FIGS. 1 to 5.

Figure 1:
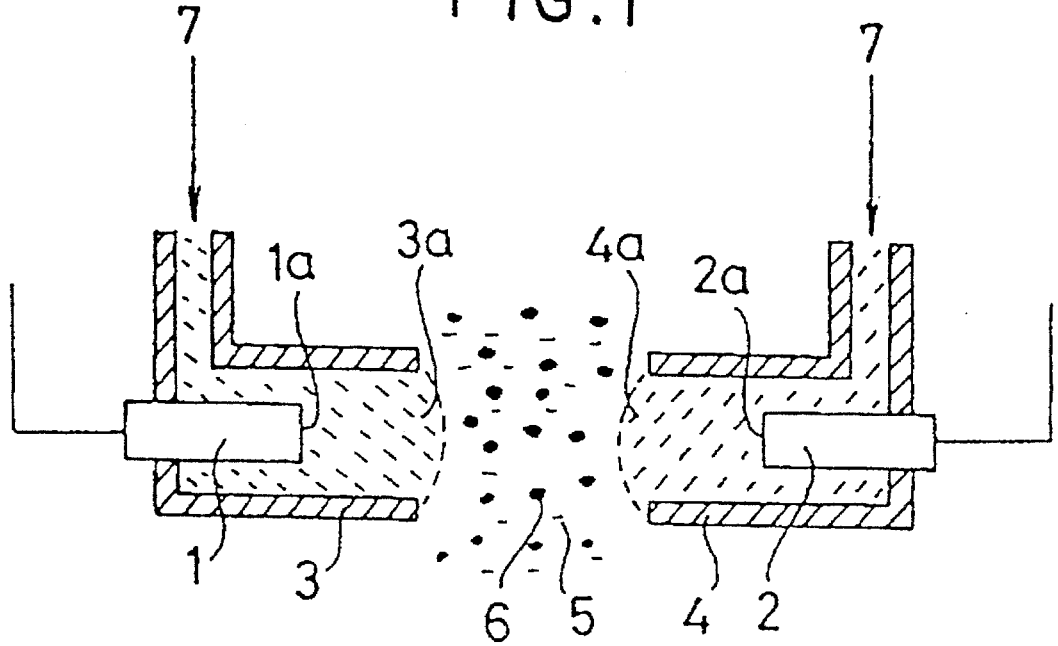
FIG. 1 is an explanatory diagram showing the measurement principle of the concentration measurement apparatus of the present invention.

In FIG. 1, reference 1 indicates a transmitter having a transmitting surface $1a$, and reference 2 indicates a receiver having a receiving surface $2a$ which is provided in opposition to transmitter 1.

The sound waves or light waves transmitted from transmitting surface $1a$ of transmitter 1 in the direction of receiving surface $2a$ of receiver 2 are attenuated and scattered by means of the suspended matter 6 which is suspended in substance 5 to be measured, and the variations in the amount thereof are detected by receiver 2. This detection signal undergoes calculation processing in a control part which is not depicted in the Figure, and is then displayed as the concentration of suspended matter.

The transmitting surface position of transmitter 1 and the receiving surface position of receiver 2 are enclosed by small pipes 3 and 4 which are opened in the direction of transmission and in the direction of reception, respectively, and the inner portions of these small pipes 3 and 4 are filled with a clean liquid 7 which is introduced thereinto. The clean liquid 7 is introduced into the inner portions of small pipes 3 and 4 at a pressure which is slightly higher than the pressure of the substance 5 to be measured at these positions, so that the inner portions are filled with clean liquid 7, and the entry of substance 5 to be measured into the inner portions of small pipes 3 and 4 does not occur. Furthermore, the clean liquid 7 flows slightly outward into substance 5 to be measured from the opening $3a$ of small pipe 3 and the opening $4a$ of small pipe 4; however, in general, the amount flowing out is slight, and there is thus no large effect on measurement accuracy.

The interior portions of small pipes 3 and 4 are filled with clean liquid 7, so that the transmitting surface $1a$ of transmitter 1 and the receiving surface $2a$ of receiver 2 do not come into direct contact with substance 5 to be measured, and accordingly, deposition or generation of contamination on transmitting surfaces $1a$ and $2a$ does not occur, and it is possible to accurately measure the concentration of suspended matter in a constant manner.

To take the example of sewage sludge as a substance to be measured, it is appropriate that water be the clean liquid filling the inner portions of small pipes 3 and 4, and in the case in which the substance to be measured is a solvent, a pure solvent of an identical type is appropriate.

According to the conditions of the placement of the concentration measuring apparatus, there is a slight possibility that the clean liquid flowing out from the small pipes 3 and 4 of the transmitter 1 and the receiver 2 will dilute the substance 5 to be measured; however, in such a case, it is possible to correct the measurement in advance from the ratio of the amounts of the clean liquid flowing out and the substance to be measured, and it is desirable to avoid errors in measurement resulting from dilution in this manner.

Figure 2:
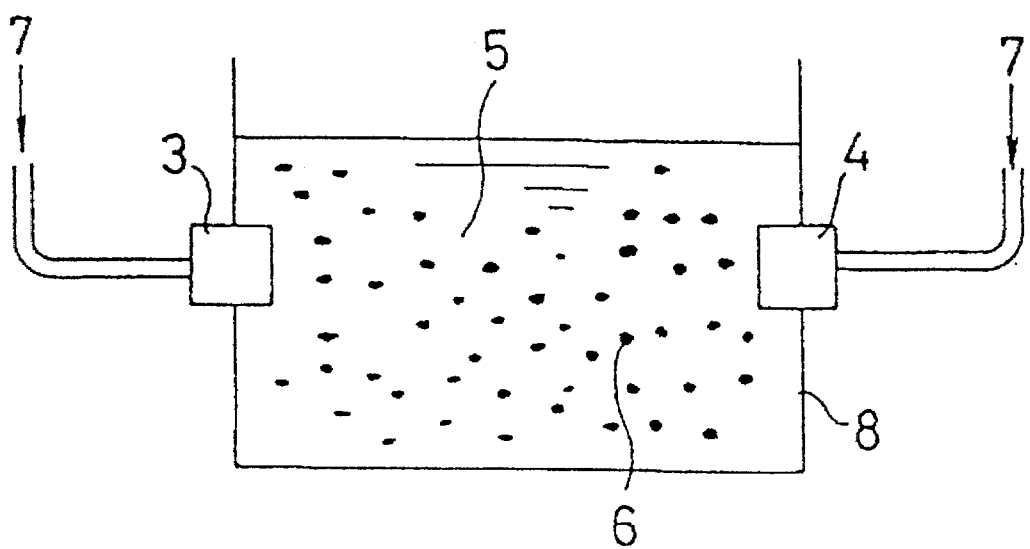
FIG. 2 is a lateral cross sectional view of a first preferred embodiment of the present invention.
Figure 3:
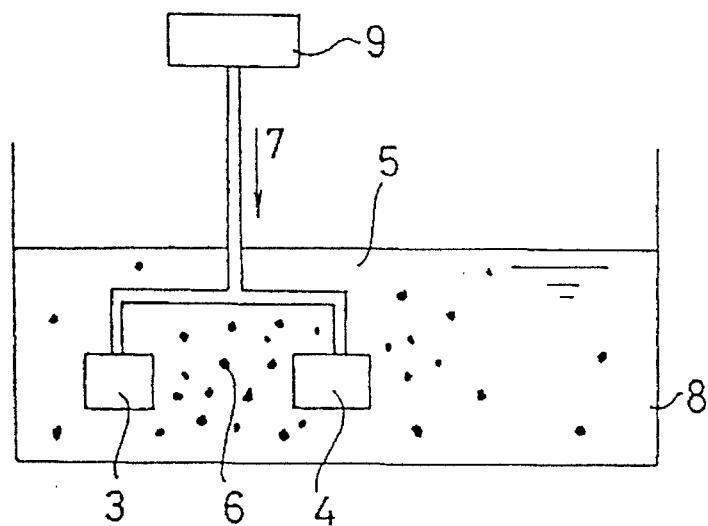
FIG. 3 is a lateral cross sectional view of a second preferred embodiment of the present invention.
Figure 4A:
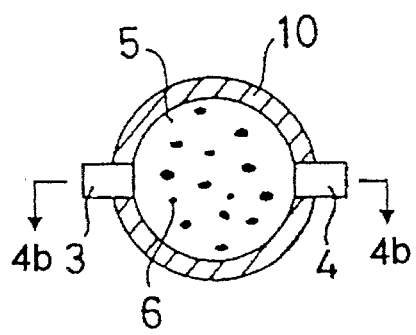
FIG. 4a is a vertical cross sectional view FIG. 4b and an upper cross sectional view of a third preferred embodiment of the present invention.
Figure 4B:
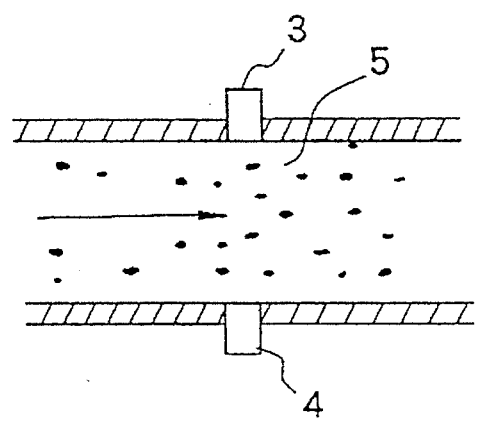

FIGS. 2, 3, and 4 all show concrete examples of the arrangement of the main parts of a concentration measurement apparatus comprising the transmitter 1 and the receiver 2 depicted in FIG. 1. FIG. 2 shows an embodiment in which the transmitter 1 and the receiver 2, which are located oppositely, are affixed to the side walls of a liquid tank 8 containing the liquid 5 which is to be measured, in which suspended matter is uniformly suspended. FIG. 3 shows an embodiment in which the mutually opposed transmitter 1 and receiver 2 are attached to an integral transportable member 9 and can be placed at a freely selected depth in liquid tank 8. FIGS. 4($a$) and ($b$) show an embodiment in which the mutually opposed transmitter 1 and receiver 2 are affixed to the walls of a pipe 10 through which the liquid 5 which is to be measured, which has suspended matter suspended uniformly therein, is flowing.

In the embodiments shown in FIGS. 2, 3, and 4, there is no change in the respective enclosure of the transmitting surface position of transmitter 1 and the receiving surface position of receiver 2, or in the filling of the inner portions of small pipes 3 and 4, which are opened in the direction of transmission and the direction of reception, respectively, with a clean liquid which is supplied thereto.

Figure 5:
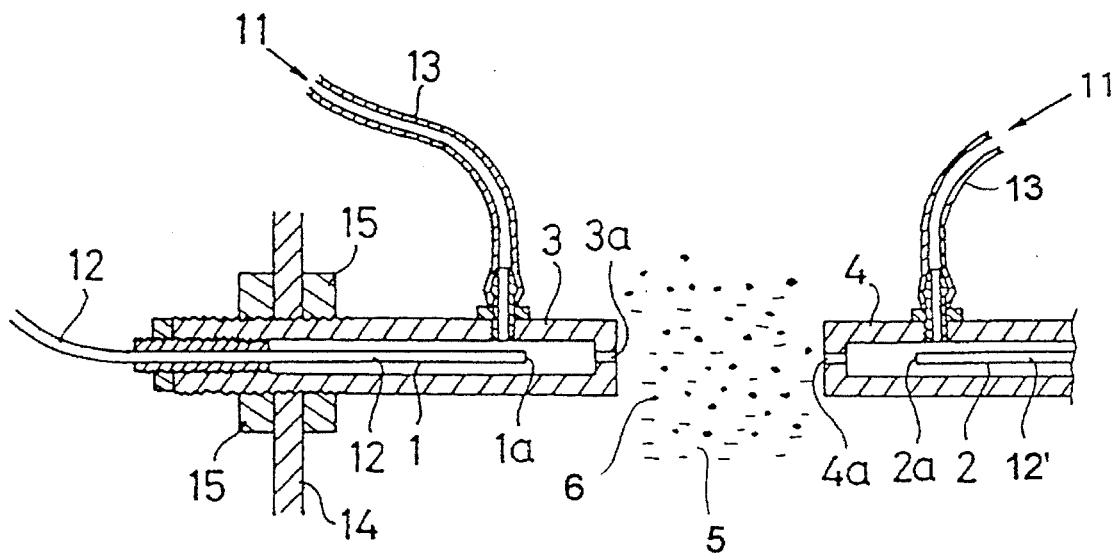
FIG. 5 is a lateral cross sectional view of a fourth preferred embodiment of the present invention.

FIG. 5 shows an embodiment, in which, in place of the clean liquid filling the small pipes in the embodiments shown in FIGS. 1 to 4, a clean gas such as air or an inert gas or the like is employed.

In FIG. 5, reference 1 indicates a transmitter having a transmitting surface $1a$ comprising an end surface of an optical fiber 12, and reference 2 indicates a receiver which is provided in a position opposition to transmitter 1 and which has a receiving surface $2a$ comprising, in the same manner, at end surface of an optical fiber 12'.

A light wave which is propagated through optical fiber 12 and which is transmitted from transmitting surface $1a$ of transmitter 1 in the direction of receiving surface $2a$ of receiver 2, is attenuated and scattered by suspended matter 6 suspended in liquid 5 to be measured, and the amount of this change is detected by receiver 2. The detection signal is supplied to a control part, not depicted in the Figure, via optical fiber 12' calculation processing, and is then displayed as the concentration of suspended matter.

The end surface of optical fiber 12 comprising the transmitting surface position of transmitter 1, and the end surface of optical fiber 12 comprising the receiving surface position of receiver 2, are enclosed in small pipes 3 and 4, respectively, which are opened in the direction of transmission and in the direction of reception, respectively, and the inner portions of these small pipes 3 and 4 are filled with a clean gas 11 such as air, inert gas, or the like, which is continuously or intermittently supplied thereinto through gas supply pipes 13. Small pipes 3 and 4 may be affixed, for example, to attachment plates 14 by means of attachment nuts 15.

The clean gas 11 is supplied into the interior of small pipes 3 and 4 at a slightly greater pressure than that of the substance 5 to be measured at these positions, so that the inner portions are filled with the clean gas 11, and there is no entry of the substance 5 to be measured into the inner portions of small pipes 3 and 4. Furthermore, the clean gas 11 flows slightly out into the substance 5 to be measured from opening 3a of small pipe 3 and opening 4a of small pipe 4 as the result of the appropriate selection of the openings of the small pipes, the supply pressure, or a continuous or intermittent supply method. However, in general, the amount which flows out is only slight, so that this does not greatly affect the measurement accuracy.

The inner portions of small pipes 3 and 4 are filled with clean gas, so that the deposition or generation of contaminants on transmitting surface 1a of transmitter 1 or receiving surface 2a of receiver 2 does not occur, and it is possible to conduct the continuous accurate measurement of the concentration of the suspended matter.

The embodiment shown in FIG. 5 can be carried out by means of an embodiment mode which is identical to those shown in FIGS. 2, 3, and 4. Furthermore, in the embodiments shown in FIGS. 2 to 5, the small pipes 3 and 4 are placed oppositely at an angle of 180°; however, it is possible to carry out the invention by placing these small pipes in mutual opposition at a freely selected angle.

INDUSTRIAL APPLICABILITY

In accordance with the present invention, in a concentration measurement apparatus for measuring the concentration of suspended matter in a substance to be measured, enclosed spaces which enclose the transmitting surface position of a transmitter and the receiving surface position of a receiver, and which are opened in the direction of transmission and in the direction of reception, respectively, are provided, and a mechanism is provided for filling the enclosed spaces which a clean liquid or gas, so that contaminants are not deposited or generated on the transmitting or receiving surfaces of the transmitter and receiver, and the invention is thus useful, as it is possible to accurately measure the concentration of suspended matter in such a manner that the amount of transmission, amount of attenuation, amount of scattering, and the like of the sound waves or light waves is unaffected by contamination.

What is claimed is:

1. A concentration measurement apparatus for measuring a suspended material contained in a liquid, comprising:

a first casing having a first inlet for introducing a gas therein, and a first outlet at one end for ejecting the gas therefrom, a transmitter situated in the first casing, said transmitter ejecting signals through the first outlet, a second casing having a second inlet for introducing a gas therein, and a second outlet at one end for ejecting the gas therefrom, said second outlet facing the first outlet, a receiver situated in the second casing, said receiver receiving the signals from the transmitter through the first and second outlets while passing through the liquid disposed between the first and second casings, and means for filling the gas to the first and second casings through the first and second inlets, said gas preventing the liquid from entering into the first and second casings through the first and second outlets so that the transmitter and the receiver can measure the suspended material directly to thereby accurately and continuously measure the suspended material.

2. A concentration measurement apparatus according to claim 1, wherein said signals are selected from the group consisting of sound waves and light waves.

3. A concentration measurement apparatus according to claim 2, wherein sizes of said first and second outlets of the first and second casings are smaller than the ends of the first and second casings so that the gases are retained inside the first and second casings.

4. A concentration measurement apparatus according to claim 3, wherein said filling means supplies the gas continuously to the first and second casings.

5. A concentration measurement apparatus according to claim 4, wherein said first and second casings are connected together with a predetermined distance away from each other so that the first and second casings can be placed in a tank.

* * * * *